United States Patent
Bartoszyk et al.

(10) Patent No.: US 7,371,756 B2
(45) Date of Patent: May 13, 2008

(54) USE OF 1-[4-(5-CYANOINDOL-3-YL)BUTYL]-4-(2-CARBAMOYL-BENZOFURAN-5-YL)-PIPERAZINE AND ITS PHYSIOLOGICALLY ACCEPTABLE SALTS

(75) Inventors: Gerd Bartoszyk, Weiterstadt (DE); Christoph Seyfried, Seeheim (DE); Christoph Von Amsterdam, Darmstadt (DE); Henning Boettcher, Darmstadt (DE); Ewen Sedman, Alresford (GB)

(73) Assignee: Merck Patent GmbH, Darmstadt (DE)

( * ) Notice: Subject to any disclaimer, the term of this patent is extended or adjusted under 35 U.S.C. 154(b) by 365 days.

(21) Appl. No.: 10/994,226

(22) Filed: Nov. 23, 2004

(65) Prior Publication Data

US 2005/0113386 A1    May 26, 2005

Related U.S. Application Data

(62) Division of application No. 09/979,922, filed as application No. PCT/EP00/04376 on May 16, 2000, now Pat. No. 6,900,212.

(30) Foreign Application Priority Data

May 27, 1999    (EP) .................................. 99109295

(51) Int. Cl.
    *A61K 31/497*    (2006.01)
(52) U.S. Cl. ................................. 514/254.09
(58) Field of Classification Search ............ 514/254.09
    See application file for complete search history.

(56) References Cited

U.S. PATENT DOCUMENTS

| 5,532,241 A | | 7/1996 | Boettcher et al. |
| 5,723,614 A | * | 3/1998 | Bathe et al. ................. 544/376 |
| 5,914,394 A | * | 6/1999 | Chen et al. ................. 536/23.5 |
| 6,900,212 B1 | * | 5/2005 | Bartoszyk et al. ..... 514/254.09 |

FOREIGN PATENT DOCUMENTS

| HU | 218 918 | 12/2000 |
| WO | WO 0006160 A | 3/1998 |

OTHER PUBLICATIONS

Dorland's Illustrated Medical Dictionary, 28th Edition, p. 1383-1384, 1994.*
Hungarian Search Report issued Feb. 17, 2004 in P0201275.
Molewijk et al., "Conditioned Ultrasonic Distress Vocalizations in Adult Male Rats as a Behavioural Paradigm for Screening Antipanic Drugs" *Psychopharmacology* (1995); 117: 32-40.

De Vry et al., "Shock-induced Ultrasonic Vocalization in Young Adult Rats: a Model for Testing Putative Anti-anxiety Drugs" *Eur J. Pharmacol* (1993); 249: 331-339.
Van Vliet et al., "Effects of the 5-HT$_{1A}$ Receptor Agonist Flesinoxan in Panic Disorder" *Psychopharmacology* (1996); 127: 174-180.
Cottraux, et al., "A Controlled Study of Cognitive Behaviour Therapy with Buspirone or Placebo in Panic Disorder with Agoraphobia" *British Journal of Psychiatry* (1995); 167, 635-641.
Zuardi, "5-HT-Related Drugs and Human Experimental Anxiety" *Neuroscience & Biobehavioral Reviews*, vol. 14, (1990); 507-510.
Kasper und Resinger, "Panic Disorder: the Place of Benzodiazepines and Selective Serotonin Reuptake Inhibitors" *Eur Neuropsychopharmacol* (2001); 11: 307-321.
Sànchez und Meier, "Behavioral Profiles of SSRIs in Animal Models of Depression, Anxiety and Aggression, Are they all alike?" *Psychopharmacology* (1997); 129:197-205.
Broocks et al., "Behavioral, Physiological and Neuroendocrine Respones in Healthy Volunteers to m-Chlorophenylpiperazine (m-CPP) with and without Ondansetron Pretreatment" *Psychopharmacology* (1997); 130: 91-103.
Sànchez et al., "Assesment of Relative Efficacies of 5-HT$_{1A}$ Recptor Ligands by Means of in Vivo Animal Models" *Eur J. Pharmacol* (1996); 315: 245-254.
Seibyl et al., "Effects of Ritanserin on the Behavioral, Neuroendocrine, and Cardiovascular Responses to Meta-Chlorophenylpiperazine in Healthy Human Subjects" *Psychiatry Res.* (1991); 38: 227-336.
Broocks et al., "Increases Psychological Responses and Divergent Neuroendocrine Responses to m-CPP and Ipsapirone in Patients with Panic Disorder" *Int Clin. Psychopharmacol* (2000); 15: 153-161.
Silverstone et al., "The Effects of Administration of mCPP on Psychological, Cognitive, Cardiovascular, Hormonal and MHPG Measurements in Human Volunteers" Int. *Clin. Psychopharmacol* (1994); 9: 173-178.

(Continued)

*Primary Examiner*—Jennifer Kim
(74) *Attorney, Agent, or Firm*—Miller, White, Zelano, Branigan, P.C.

(57) ABSTRACT

1-[4-(5-cyanoindol-3-yl)butyl]-4-(2-carbamoyl-benzofuran-5-yl)-piperazine or a physiologically acceptable salt thereof, for the treatment of sub-type anxiety disorders chosen from the sub-types: panic disorder with or without agoraphobia, agoraphobia, obsessive-compulsive spectrum disorders, social phobia, posttraumatic stress disorder, acute stress indication or generalized anxiety disorder, bipolar disorders, mania, dementia, substance-related disorders, sexual dysfunctions, eating disorders, obesity, anorexia, and fibromyalgia. A preferred salt is 1-[4-(5-cyanoindol-3-yl)butyl]-4-(2-carbamoyl-benzofuran-5-yl)-piperazine hydrochloride.

16 Claims, No Drawings

OTHER PUBLICATIONS

Pols et al., "Yohimbine Premedication and 35% $CO_2$ Vulnerability in Healthy Volunteers" *Eur Arch Psychiatry Clin. Neurosci* (1994); 244: 81-85.

Lesch, et al., "5-$HT_{1A}$ Receptor-effector System Responsivity in Panic Disorder" *Psychopharmacology* (1992); 106: 111-117.

Charney, et al., "Serotonin Function in Anxiety" *Psychopharmacology* (1987); 92: 14-24.

Pohl, et al., "Serotonergic Anxiolytics in the Treatment of Panic Disorder: A Controlled Study with Buspirone" *Psychopathology* (1989); 22 (suppl. 1):60-67.

Sheehan, et al., "The Relative Efficacy of High-dose Buspirone and Alprazolam in the Treatment of Panic Disorder: A Double-Blind Placebo-controlled Study" *Acta Psychiatr Scand* (1993); 88: 1-11.

Sheehnan, et al., "Is Buspirone Effective for Panic Disorder?" *Journal of Clinical Psychopharmacology* (1990); vol. 10, No. 1:3-11.

Napoliello, et al., Buspirone: A Worldwide Update *British Journal of Psychiatry* (1991); 159 (suppl. 12), 40-44.

Sànchez et al., "Effect of Serotonergic Drugs on Footshock-induced Ultrasonic Vocalization in Adult Male Rats" *Behavioural Pharmacology* (1993);.4, 269-277.

Bourin et al., Provactive Agents in Panic Disorder: *Thérapie* (1995); 50: 301-306.

Bartoszyk G D et al.: "Emd 68843, A Seritonin Reuptake Inhibitor With Selective Presynaptic 5-Ht1a Receptor Agonistic Properties" European Journal Of Pharmacology, Amsterdan, NL, vol. 322, Mar. 1997, pp. 147-153, XP000917722 ISSN: 0014-2999.

DSM-IV, Online Psychological Services, PsychologyNet.org, list of mental disorders, 1994, 1-3.

\* cited by examiner

USE OF 1-[4-(5-CYANOINDOL-3-YL)BUTYL]-4-(2-CARBAMOYL-BENZOFURAN-5-YL)-PIPERAZINE AND ITS PHYSIOLOGICALLY ACCEPTABLE SALTS

This application is a divisional of U.S. application Ser. No. 09/979,922, filed Apr. 8, 2002, now U.S. Pat. No. 6,900,212, which claimed priority of EP 99 109295.8, filed May 27, 1999, and which is a 371 of PCT/EP00/04376, filed May 16, 2000.

The present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of sub-type anxiety disorders.

1-[4-(5-cyanoindol-3-yl)butyl]-4-(2-carbamoyl-benzofuran-5-yl)-piperazine, physiologically acceptable salts thereof (U.S. Pat. No. 5,532,241, column 7, lines 30 to 58) and a process (U.S. Pat. No. 5,532,241, Example 4) by which it/they can be prepared are known from U.S. Pat. No. 5,532,241. The compound which is referred to herein is described in the patent as a combined selective serotonin (5-HT) reuptake inhibitor (SSRI) and $5\text{-HT}_{1A}$ receptor agonist. Therefore, the use of 1-[4-(5-cyanoindol-3-yl)butyl]-4-(2-carbamoyl-benzofuran-5-yl)-piperazine and its physiologically acceptable acid addition salts for the manufacture of a medicament for the treatment of depressive disorders, including the sub-type disorders major depressive disorder and dysthymic disorder, for the treatment of anxiety disorders, for the treatment of psychiatric disorders like psychoses, schizophrenia or schizoaffective disorder, for the treatment of cerebral infarct like stroke and cerebral ischemia, for the treatment of CNS disorders such as tension, for the therapy of side-effects in the treatment of hypertension (e.g. with α-methyldopa) and for the prophylaxis and therapy of cerebral disorders (e.g. migraine) is disclosed. Additionally, the use in endocrinology and gynecology is described, e.g. for the treatment of acromegaly, hypogonadism, secondary amenorrhea, premenstrual syndrome or undesired puerperal lactation.

Furthermore, it is known that they have a useful potential utility for the treatment of sleep disorders, including dyssomnias and narcolepsy.

The invention had the object of providing novel uses for 1-[4-(5-cyanoindol-3-yl)butyl]-4-(2-carbamoyl-benzofuran-5-yl)-piperazine and its physiologically acceptable salts having significantly better pharmacological properties than compounds of the prior art.

It has been found that 1-[4-(5-cyanoindol-3-yl)butyl]-4-(2-carbamoyl-benzofuran-5-yl)-piperazine also has activity against sub-type anxiety disorders chosen from the sub-types panic disorder with and/or without agoraphobia, agoraphobia, obsessive-compulsive spectrum disorders, social phobia, specific phobia including neophobia, posttraumatic stress disorder, acute stress indication or generalized-anxiety disorder.

Accordingly, the present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of sub-type anxiety disorders chosen from the sub-types panic disorder with or without agoraphobia, agoraphobia, obsessive-compulsive spectrum disorders including obsessive compulsive disorders, social phobia, specific phobia including neophobia, posttraumatic stress disorder, acute stress indication and/or generalized-anxiety disorder.

It is known that 5-HT reuptake inhibitors such as fluoxetine (L. Solyom, C. Solyom, B. Ledwidge, Can. J. Psychiatry, 1991, 36: 378-380) or $5\text{-HT}_{1A}$ receptor agonists such as geprione (J. C. Pecknold, L. Luthe, M. H. Scott-Fleury, S. Jenkins, J. Clin. Psychopharmacology, 1993, 13: 145-149) are clinically effective in panic disorders. It has been found that a combined elective 5-HT reuptake inhibitor and $5\text{-HT}_{1A}$ receptor agonist which includes both mechanisms leads to an advantage in clinical practice.

A typical model for panic disorder is the Mouse Defense Test Battery according to G. Griebel, D. C. Blanchard, R. J. Blanchard, Prog. Neuropsychopharmacol. & Biol. Psychiat, 1996, 20: 185-205. The mouse defence battery test consists of an oval runway of 2 m straight segments joint by two 0.4 m curved segments separated by a median wall. A mouse is placed in the runway for a 3 min familiarization period. Then, a hand-held anaesthetized rat is introduced into the runway and brought up to the mouse. Approach is terminated when contact with the mouse was made or the mouse runs away from the approaching rat. If the subject runs away, avoidance distance and the number of avoidances after five approaches are recorded. Immediately after these approaches, the rat chases the mouse for a distance of 15 m, and flight speed is recorded.

A typical model for Agoraphobia is named Elevated Plus Maze according to S. Pellow, P. Chopin, S. E. File, M. Briley, J. Neurosci. Meth., 1985, 14: 145-167.

The apparatus consists of an X-shaped platform elevated from the floor, with two "open" unprotected arms and two "closed" protected arms, with animals having free access to both arms. The rat or mouse is placed in the centre of the arms, and the number of entires made and the time spent on the open arms is measured in a 3 min test period. Normal animals have very low basal levels, i.e. avoid entering the open arms and stay only a for a very brief period on open arms.

1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, following oral application dose-dependently increased both the number of entries and the time spend on open arms. For example, in mice the dose of 10 mg/kg p.o. increased the number of entires by 157% and time spent on open arms by 105%. In rats, a dose of 10 mg/kg p.o. increased number of entries by 56% and time spent on open arms by 76%.

It is known that 5-HT reuptake inhibitors such as paroxetine (A. K. Cardogan, I. K. Wright, I. Combs, C. A. Marsden, D. A. Kendall, I. Tulloch, Neurosci. Lett. 42: S8) or $5\text{-HT}_{1A}$ receptor agonists such as geprione (V. Motta, S. Maisonnette; S. Morato; P. Castrechini; M. L. Brandao, Psychopharmacology, 1992; 107: 135-139) or 8-OH-DPAT (8-hydroxy-dipropylaminotetralin) (N. Collinson, G. R. Dawson, Psychopharmacology, 1997, 132: 35-43) have been shown to be effective in the elevated plus maze test. It has been found that a combined selective 5-HT reuptake inhibitor and $5\text{-HT}_{1A}$ receptor agonist which includes both mechanisms leads to therapeutic advantages.

Obsessive Compulsive Disorders (OCDs) are characterized by unwanted intrusive, recurring thoughts, images, or actions which generate an irrational dread (obsession) of germs, dirt, contamination, apprehension of acting on violent or aggressive impulses, feeling overly responsible for the safety of others, e.g. unreasonable dread of having run over someone with a car, abhorrent religious (blasphemous)

and sexual thoughts, inordinate concern with order, arrangement, or symmetry, inability to discard useless or worn out possessions.

This often results in the repetitive performance of rituals (compulsions), such as excessive washing (particularly hand-washing or bathing), touching, counting, arranging and ordering, checking, cleaning and hoarding which persons suffering from OCD feel they can not control. Performing these rituals, however, provides only temporary relief. This person is almost always aware that their strange compulsive behaviour makes no sense, but feels helpless to stop it. This person can have a few or many of these symptoms, which can vary during the course of the disorder. The patterns may be repeated as much as 100 times or for several hours per day, and renders the person unable to function normally (for review e.g. Dolberg et al., Clin. Neuropharmacol. 1996, 19: 129 or F. Tallis, Br. J. Clin. Psychol. 1997, 36: 3).

Obsessive Compulsive Spectrum Disorders (OCSDs) share common features with OCDs including overlapping symptom profiles, demographics, family history, comorbidity, clinical course and response to anti-obsessional treatment.

OCSDs include e.g. somatoform disorders (e.g. body dysmorphobia, hypochondriasis), tic disorders (e.g. Gilles de la Tourette's syndrome), impulsive personality disorders (e.g. antisocial personality disorder), impulse control disorders (e.g. trichotillomania, kleptomania, pyromania, pathological gambling, sexual compulsions such as exhibitionism, voyeurism, fetishism), schizo-obsessive disorders(e.g. obsessional schizophrenia, schizotypic OCD, delusional OCD), dissociative disorders (e.g. autism, torticolis, Sydenham's Chorea, Asperger's syndrome) [for review e.g. E. Hollander and C. Wong, J. Clin. Psychiatry 1995, 56 (suppl. 4): 3 or McElroy et al., J. Clin. Psychiatry 1994, 55 (suppl. 10): 33].

A typical model for OCSD including OCD is the Marble Burying Test according to Y. Ichimaru, T. Egawa, A. Sawa, Jpn. J. Pharmacol. 1995, 68: 65-70.

The apparatus consists of an open cubic box with 25 clean glass marbles evenly spaced on sawdust. Individual mice are placed in the test box, and the number of glass marbles left uncovered after 20 minutes are counted. 1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, following subcutaneous application inhibits mable burying in mice dose-dependently. For example, a dose of 3 mg/kg of 1-[4(5-cyanoindol-3-yl)butyl]-4-(2-carbamoyl-benzofuran-5-yl)-piperazine hydrochloride nearly completely (92%) inhibits marble burying; equieffective doses of conventional serotonin reuptake inhibitors are e.g. 20 mg/kg for fluvoxamine or 17 mg/kg for fluoxetine and an equieffective dose of the 5-$HT_{1A}$ agonist ipsapirone is 10 mg/kg.

It is known that 5-HT reuptake inhibitors or 5-$HT_{1A}$ receptor agonists inhibit marble burying, e.g. fluvoxamine, citalopram or 8-OH-DAPT, gepirone (K. Njung'e, S. L. Handley, Br. J. Pharmacol., 104: 105-112;). So-far the selective serotonine reuptake inhibitors (SSRIs) are chosen for the treatment of OCSD (W. K. Goodman, L. H. Price, P. L. Delgado, Arch. Gen. Psychiatry 1990, 47: 577-585). It has been found that a combined selective 5-HT reuptake inhibitor and 5-$HT_{1A}$ receptor agonist has an increased activity and a faster onset of action.

A model for social phobia is the Social Interaction Test according to S. File, J. R. G Hyde, J. Pharm. Pharmacol. 1977, 29: 735-738.

Pairs of rats not familiar with each other are placed in an open test box brightly lit (aversive condition), and the number and duration of social contacts during a 5 min test session are recorded.

1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, increase the time spent in social interaction. For example, for an oral dose of 10 mg/kg of 1-[4-(5-cyanoindol-3-yl)butyl]-4-(2-carbamoyl-benzofuran-5-yl)-piperazine hydrochloride the pairs of rats unfamiliar to each other spend 144 sec of the 300 sec of total time with social interaction compared to 116 sec for the vehicle treated pairs of rats.

It is known that the 5-HT reuptake inhibitor paroxetine (S. Lightowler, I. J. R. Williamson, J. Hegarty, G. A. Kennett, R. B. Fears, I. F. Tulloch, Br. J. Pharmacol. 1992, 106: 44P) or the 5-$HT_{1A}$ receptor agonists 8-OH-DPAT or ipsapirone (G. A. Higgins; A. J. Bradbury; B. J. Jones; N. R. Oakley, Neuropharmacology, 1988, 27: 993-1001) increase social interaction behaviour. It has been found that a combined selective 5-HT reuptake inhibitor and 5-$HT_{1A}$ receptor which includes both mechanisms leads to therapeutic advantages.

A model for specific phobia is the Shock-Probe Test according to D. Treit, M. A. Fundytus, Pharmacol. Biochem. Behav. 1988, 30: 1071-1075. Individual rats are habituated for 30 min each of 4 days to an open box filled with sawdust. On the test day, a continuously electrified probe is inserted 2 cm above the ground. The number of contacts with the probe is counted and the attemps to cover the probe with sawdust are recorded.

It is known that the serotonin reuptake inhibitor imipramine (T. F. Meert, F. C. Colpaert, Psychopharmacology, 1986, 88: 445-450) or 5-$HT_{1A}$ receptor agonists, e.g. 8-OH-DPAT (D. Treit; A. Robinson; S. Rotzinger; C. Pesold, Behav-Brain-Res., 1993, 54: 23-34) or ipsapirone (S. M. Korte, B. Bohus, Eur. J. Pharmacol., 1990, 181: 307-10) demonstrated efficacy in this model. It has been found that a combined selective 5-HT reuptake inhibitor and 5-$HT_{1A}$ receptor which includes both mechanisms leads to therapeutic advantages.

In a typical model for neophobia, mice deprived from food for 18 h are given access to unfamiliar food in a novel environment [P. Soubrie et al., Psychopharmacologica, 1975, 45: 203-210]. 1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, following oral application increased food intake by 21% at the dose of 3 mg/kg.

Animal models of anxiety associated with posttraumatic stress in rats utilize the long-lasting behavioural changes induced by exposure to a native stressor. The therapeutic effects of a compound effective for the acute treatment of anxiety associated with posttraumatic stress are modelled by administration of the compound after exposure to the stressor. The therapeutic effects of a compound effective for the prophylactic treatment of anxiety associated with posttraumatic stress are modelled by administration of the compound before exposure to the stressor. Amongst the several behavioral test procedures, the following is most validated [R. E. Adamec and T. Shallow, Physiology Behavior, 1993, 54: 101-109; R. E. Adamec et al., Behav. Neurosci. 1997, 111: 435-449]. In general, a rat is exposed to a cat for five minutes, and seven days later the rat can be tested in a battery of tests, i.e. the hole board test, the elevated plus maze and the acoustic startle test. The hole board consists of a box (60 cm×60 cm) with four evenly spaced holes; the number of poking its head into a hole is counted for 5 minutes. The elevated plus maze consists of an X-shaped platform elevated from the floor, with two "open" unprotected arms and two "closed" protected arms, with rats having free access to both arms. The rat is placed in the centre of the arms, and the frequency of attempts to enter an open arm (risk assessment) as well as the time spent on the open and closed arms are measured. In the acoustic startle test, the rat is placed in a plexiglass cylinder, and a series of 20 white noise bursts of 120 dB out of a background noise of 60 dB is applied, and the latency to and the peak startle amplitude are measured. In general, rats exposed to the a stressor like a cat show a reduced number of head dips into the holes, have a lower risk assessment and spend less time on the open arms, and the startle response is increased.

1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, are effective in the models for anxiety associated with posttraumatic stress when given after (acute treatment) and before (prophylactic treatment) the cat stressor.

A typical clinical study for post traumatic stress disorder is described in the following.

Twenty (20) male or female patients aged 18-65 years suffering from non-combat related chronic post traumatic stress disorder as defined by DSM-IV (Diagnostic and Statistical Manual for Mental Disorders, Fourth Version) will be treated for a 12 week period. Ten patients will be assigned randomly to receive 1-[4-(5-cyanoindol-3-yl)butyl]-4-(2-carbamoyl-benzofuran-5-yl)-piperazine or a physiologically acceptable salt thereof and 10 patients will receive matched placebo in a double-blind fashion.

Outcome will be assessed by the treating physician and the patient with the use of the Hamilton Depression Rating Scale, the Montgomery-Asberg Depression Rating Scale, The Clinical and Patient Global Impression Scales, general symptoms and specific rating of PTSD core symptoms using the Clinician Administered PTSD Scale according to D. Blake et al, Behavioral Therapy 1990, 13: 187-188 and TOP-8 scale according to J. R. T. Davidson et al, International Clinical Psychopharmacology 1997, 12: 41-45.

A typical model for acute stress indication is the Four Plate Test according to C. Aron, P. Simon, C. Larousse, J. R. Boissier, Neuropharmacology 1971, 10: 459-469.

The apparatus consists of small box with a floor made up of four metal plates. Each time the mouse crosses from one plate to another, it is given a brief electric footshock reducing the amount of exploratory behavior. The number of punished crossings from one plate to another (i.e. number of shocks accepted by the animal) is recorded during a five minute test period. Normal mice make only few punished crossings, i.e. accept only a few footshocks.

1-[4-(5-cyanoindol-3-yl)butyl]-4-(2-carbamoyl-benzofuran-5-yl)-piperazine hydrochloride following and oral dose of 3 mg/kg increased the number of punished crossings by 41%.

This model has been validated with clinically active benzodiazepines in the literature (e.g. D. N. Stephens, W. Kehr, Psychopharmacology 1985, 85: 143-147; G. D. Bartoszyk, U. Schoenherr, Behav. Neural Biol. 1987, 48: 317-9). It has been found that a combined selective 5-HT reuptake inhibitor and 5-$HT_{1A}$ receptor leads to therapeutic advantages because it avoids the sedative properties of benzodiazepines.

A typical model for generalized anxiety disorders is the Light-Dark Choise Test (Passive Avoidance Test) according to J. N. Crawly, Pharmacol. Biochem Behav. 1981, 15: 695-699.

The light-dark choise apparatus consists of two connected boxes with one box darkened and the other one highly illuminated. A mouse is placed in one box, and the time spent in lit box and the number of transitions between boxes are measured over a period of 5 min. Normal mice only have low numbers of entries to the lit compartment and spent most time in the dark compartment.

1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, following oral application dose-dependently increase the number of transitions and time spent in lit compartment. For example, an oral dose of 10 mg/kg of 1-[4-(5-cyanoindol-3-yl)butyl]-4-(2-carbamoyl-benzofuran-5-yl)-piperazine hydrochloride increased the number of transitions by 73% and time spent in lit compartment by 31%.

It is known from the 5-HT reuptake inhibitors, imipramine (R. Young, D. N. Johnson, Pharmacol. Biochem. Behav., 1991, 40: 739-743), or the 5-$HT_{1A}$ receptor agonists e.g. 8-OH-DPAT and ipsapirone (B. Costall; A. M. Domeney, A. J. Farre; M. E. Kelly; L. Martinez; R. J. Naylor, J. Pharmacol. Exp. Ther., 1992, 262: 90-98) that they increase time spent in illuminated compartment and number of transitions between compartments. It has been found that a combined selective 5-HT reuptake inhibitor and 5-$HT_{1A}$ receptor which includes both mechanisms leads to therapeutic advantages.

A preferred salt of 1-[4-(5-cyanoindol-3-yl)butyl]-4-(2-carbamoyl-benzofuran-5-yl)-piperazine is 1-[4-(5-cyanoindol-3-yl)butyl]-4-(2-carbamoyl-benzofuran-5-yl)-piperazine hydrochloride.

Therefore the invention relates to the use for the manufacture of a medicament for the treatment of sub-type anxiety disorders in which the pharmacologically acceptable salt is 1-[4-(5-cyanoindol-3-yl)butyl]-4-(2-carbamoyl-benzofuran-5-yl)-piperazine hydrochloride.

Additionally, the invention relates to the use of a pharmaceutical composition containing at least one compound of 1-[4-(5-cyanoindol-3-yl)butyl]-4-(2-carbamoyl-benzofuran-5-yl)-piperazine and/or one of its biocompatible salts together with at least one solid, liquid or semiliquid excipient or adjunct for the treatment of sub-type anxiety disorders chosen from the sub-types panic disorder with and/or without agoraphobia, agoraphobia, obsessive-compulsive spectrum disorders, social phobia, specific phobia including neophobia, posttraumatic stress disorder, acute stress indication or generalized-anxiety disorder.

Thus the invention provides a pharmaceutical preparation for the treatment of such sub-type anxiety disorders characterized in that it contains at least 1-[4-(5-cyanoindol-3-yl) butyl]-4-(2-carbamoyl-benzofuran-5-yl)-piperazine or one of its pharmaceutically acceptable salts.

The compounds, 1-[4-(5-cyanoindol-3-yl)butyl]-4-(2-carbamoyl-benzofuran-5-yl)-piperazine and its pharmaceutically acceptable salts, according to the invention are preferably administered in analogy to other known commercially available preparations for the treatment of sub-type anxiety disorders (e.g. fluoxetine, fluvoxamine). A unit dose will generally contain from 0.1 to 1000 mg, preferably between approximately 0.1 and 500 mg, in particular 5, 10, 20, 30, 40, 50, 100, 150, 200, 250 and 300 mg. The composition may be administered once or more times a day for example 2, 3 or 4 times daily. The daily dose is preferably between approximately 0.01 and 50 mg/kg of body weight. However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. Oral administration is preferred, but also peroral routes of administration (e.g. intraveneous or transdermal) can be utilized.

Additionally, it has been surprisingly found that 1-[4-(5-cyanoindol-3-yl)butyl]-4-(2-carbamoyl-benzofuran-5-yl)-piperazine also has activity against bipolar disorders and/or mania.

A typical animal model of mania/bipolar disorders is the hyperactivity induced by a mixture of dexamphetamine and chlordiazepoxide according to A. L. Vale and F. Ratcliffe, Psychopharmacology, 1987; 91: 352-355. and B. J. Cao and N. A. Peng, Eur. J. Pharmacol., 1993; 237: 177-181. The dexamphetamine-chlordiazepoxide mixture induces strong hyperactivity in mice or rats.

1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, inhibit the hyperactivity induced by the mixture to the same degree as do lithium and valproate, the standard treatments for mania and bipolar disorders.

Accordingly, the present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of bipolar disorders and/or mania.

A typical clinical study for bipolar disorders and/or mania is described in the following.

Twenty (20) male or female patients aged 18-65 years suffering from an acute hypomanic episode as part of a Bipolar II Disorder as diagnosed by DSM-IV will be treated for a 3 week period with either 1-[4-(5-cyanoindol-3-yl) butyl]-4-(2-carbamoyl-benzofuran-5-yl)-piperazine or one of its physiologically acceptable salts or lithium in a double-blind fashion.

Clinical improvement will be assessed by means of the Mania sub-scale of the SADS-C according to R. R. Lewine et al., Schizophr. Bull. 1983, 9(3): 368-76, the Young Mania Rating Scale according to R. G. Cooke et al, Biol-Psychiatry. 1996, 40(4): 279-83, the Hamilton Depression Rating Scale according to M. Hamilton, Journal of Neurology, Neurosurgery and Psychiatry 1960, 23: 56-62, the Global Assessment Scale according to J. Endicott et al., Arch. Gen. Psychiatry, 1976, 33(6): 766-71 and the Clinical Global Improvement Scale according to W. Guy (ed.), ECDEU Assessment for Psychopharmacology, 1976, 217-222 at weekly intervals. The results of this study will be used to determine if 1-[4-(5-cyanoindol-3-yl)butyl]-4-(2-carbamoyl-benzofuran-5-yl)-piperazine or one of its physiologically acceptable salts exhibit acute anti-manic properties, prior to a long-term prophylaxis study.

The invention relates furthermore to the use for the manufacture of a medicament for the treatment of bipolar disorders and/or mania in which the pharmacologically acceptable salt is 1-[4-(5-cyanoindol-3-yl)butyl]-4-(2-carbamoyl-benzofuran-5-yl)-piperazine hydrochloride.

Thus the invention relates to the use of a pharmaceutical composition containing at least one compound of 1-[4-(5-cyanoindol-3-yl)butyl]-4-(2-carbamoyl-benzofuran-5-yl)-piperazine and/or one of its biocompatible salts together with at least one solid, liquid or semiliquid excipient or adjunct for the treatment of bipolar disorders and/or mania.

Thus the invention provides a pharmaceutical preparation for the treatment of bipolar disorders and/or mania characterized in that it contains at least 1-[4-(5-cyanoindol-3-yl) butyl]-4-(2-carbamoyl-benzofuran-5-yl)-piperazine or one of its pharmaceutically acceptable salts.

The compounds according to the invention are preferably administered in analogy to other known commercially available preparations for the treatment of bipolar disorders and/or mania (e.g. fluoxetine, fluvoxamine), preferably in doses of between approximately 0.1 and 500 mg, in particular between 5 and 300 mg per dose unit. The daily dose is preferably between approximately 0.01 and 10 mg/kg of body weight. However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. Oral administration is preferred, but also peroral routes of administration (e.g. intraveneous or transdermal) can be utilized.

Additionally, it has been surprisingly found that 1-[4-(5-cyanoindol-3-yl)butyl]-4-(2-carbamoyl-benzofuran-5-yl)-piperazine also has activity against dementia, including Alzheimer's disease and multi-infarct.

Accordingly, the present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of dementia.

Typical models for dementia, Alzheimer's disease and multi-infarct are the Passive Avoidance test in rats [S. D. Glick and B. Zimmerberg, Behav. Biol., 1972, 7: 245-254; D. K. Rush, Behav. Neural Biol., 1988, 50: 255-274] and the testing of memory functions in the Morris Water Maze in aged rats [R. Morris, J. Neurosci. Methods, 1984, 11: 47-60; F. H. Gage et al.; Neurobiol. Aging. 1984, 5: 43-48].

For the Passive Avoidance test, the apparatus is a runway separated from a dark compartment by a small door. The amnestic drug scopolamine is administerd before the animal is submitted to an aquisition trial: the rat is placed on the entry of the runway opposite to the dark compartment, the latency to enter the dark compartment is recorded, and once the rat has entered the dark compartment, the door is closed and a foot schock is administered via the gridfloor. A retention trial is performed 48 h later identical to the aquisition trial (without scopolamine) and the latency to enter the dark compartment recorded again. Normal scopolamine-treated animals do not remember the foot shock from the aquisition trial and enter the compartment with similar latencies in the retention trial.

1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, following oral application of 10 mg/kg p.o. enhanced memory, i.e. the latency to enter the dark compartment in the first retention trial was increased by 78% compared to untreated rats.

It is known that serotonin reuptake inhibitors such as fluoxetine counteract scopolamine-induced cognitive deficits-(S. Kumar, S. K. Kulkami, Indian J. Exp. Biol., 1996, 34: 431-435), and the involvement of 5-$HT_{1A}$ receptors in the dorsal raphe has been demonstrated (M. Carli, P.

Bonalumi, R. Samanin, Eur. J. Neurosci. 1998, 10: 221-30). It has been found that a combined selective 5-HT reuptake inhibitor and 5-HT$_{1A}$ receptor devoid of cholinergic properties leads to a major therapeutic advancement.

The Morris Water Maze consists of a circular water tank (150 cm in diameter) filled with water with an escape platform (15 cm in diameter) 18 cm from the periphery beneath the surface of the water. The water is made opaque rendering the platform invisible. Rats placed in the tank swim around and find the hidden platform accidently after a certain time (latency), and the latency to find the platform is taken as measure. When given further training session to find the platform, rats show reduced latencies from day to day, i.e. remember (learn) the location of the platform. But compared to young rats, aged rats perform less well in learning over days reflecting impaired learning capacity. Drugs effective for dementia and particularly Alsheimers disease improve the learning capacity of aged rats.

1-[4-(5-cyanoindol-3-yl)butyl]-4-(2-carbamoyl-benzofuran-5-yl)-piperazine hydrochloride is adminstered to old rats at oral doses of 1 and 3 mg/kg every day. When tested at day 7, the latencies to find the platform in the first attempt are 77 sec (1 mg/kg) and 73 sec (3 mg/kg) not differing from vehicle treated young rats (76 sec) whereas untreated old rats needed 95 sec to find the platform.

The invention relates furthermore to the use for the manufacture of a medicament for the treatment of dementia in which the pharmacologically acceptable salt is 1-[4-(5-cyanoindol-3-yl)butyl]-4-(2-carbamoyl-benzofuran-5-yl)-piperazine hydrochloride.

Furthermore, the invention relates to the use of a pharmaceutical composition containing at least one compound of 1-[4-(5-cyanoindol-3-yl)butyl]-4-(2-carbamoyl-benzofuran-5-yl)-piperazine and/or one of its biocompatible salts together with at least one solid, liquid or semiliquid excipient or adjunct for the treatment of dementia.

Thus the invention provides a pharmaceutical preparation for the treatment of dementia characterized in that it contains at least 1-[4-(5-cyanoindol-3-yl)butyl]-4-(2-carbamoyl-benzofuran-5-yl)-piperazine or one of its pharmaceutically acceptable salts.

The compounds according to the invention are preferably administered in analogy to other known commercially available preparations for the treatment of dementia including Alzheimer's disease and multi-infarct (e.g. fluoxetine, fluvoxamine), preferably in doses of between approximately 0.1 and 500 mg, in particular between 5 and 300 mg per dose unit. The daily dose is preferably between approximately 0.01 and 50 mg/kg of body weight. However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. Oral administration is preferred, but also peroral routes of administration (e.g. intraveneous or transdermal) can be utilized.

Additionally, it has been surprisingly found that 1-[4-(5-cyanoindol-3-yl)butyl]-4-(2-carbamoyl-benzofuran-5-yl)-piperazine also has activity against substance-related disorders.

Accordingly, the present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of substance-related disorders.

Substance-related disorders include substance dependence with or without its withdrawal symptoms, substance-induced mood disorder and substance-induced anxiety disorder. "Substance" is herein defined as alcohol, amphetamine, cannabis, cocaine, hallucinogen, opoid, phencyclidine, nicotine and/or tobacco for substance dependence. "Substance" is defined as alcohol, amphetamine, cocaine, hallucinogen, inhalant, opoid and/or phencyclidine for substance-induced mood disorder and for substance-induced anxiety disorder.

It has been found that 1-[4-(5-cyanoindol-3-yl)butyl]-4-(2-carbamoyl-benzofuran-5-yl)-piperazine is preferably active against alcohol-dependance and/or against nicotine (tobacco) withdrawal symptoms. Nicotine withdrawal symptoms include restlessness, irritability, drowsiness, increasingly frequent wakings from sleep, impatience, confusion, impaired concentration, carbohydrate craving and weight gain, impaired reaction time and a craving for tobacco.

In particular, 1-[4-(5-cyanoindol-3-yl)butyl]-4-(2-carbamoyl-benzofuran-5-yl)-piperazine is active against alcohol-dependence.

It is known that increased synaptic 5-HT content effectively reduces alcohol consumption in alcohol-preferring rats (F. C. Zhou, D. L. McKinzie, T. D. Patel, Li Lumeng, T. K. Li, Alcohol Clin Exp. Res. 1998, 22 (1): 266-269.) Accordingly, alcohol-preferring rats were treated with the test compound twice daily subcutaneously. Ethanol drinking, water intake and bodyweight were determined over 24 h. Baseline ethanol intake was derived from the mean ethanol intakes of the three previous non-drug days.

The invention relates furthermore to the use for the manufacture of a medicament for the treatment of substance-related disorders in which the pharmacologically acceptable salt is 1-[4-(5-cyanoindol-3-yl)butyl]-4-(2-carbamoyl-benzofuran-5-yl)-piperazine hydrochloride.

A typical animal model is the drug discrimination procedure in rats using cocaine as the stimulus cue (e.g. D. M. Wood and M. W. Emmett-Oglesby, J. Pharmacol. Exp. Ther., 1986; 237: 120-125; D. Huang and M. C. Wilson, Pharmacol. Biochem. Behav., 1986; 24: 205-210; J. M. Witkin at al., J. Pharmacol. Exp. Ther., 1991; 257: 706-713). Rats are trained to discriminate 10 mg/kg cocaine from saline in a two-lever discrimination procedure. Compounds which substitute for cocaine produce a dose-dependent increase in cocaine-appropriate responding, i.e. in selecting the cocaine-paired lever.

1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, dose-dependently but only partially substituted for cocaine (maximally 60% choise of cocaine-paired lever at 50 mg/kg p.o.). Because 1-[4-(5-cyanoindol-3-yl)butyl]-4-(2-carbamoyl-benzofuran-5-yl)-piperazine hydrochloride in contrast to cocaine does not serve as a stimulus drug by itself indicating lack of abuse potential, the generalzation to cocaine indicates therapeutic benefit.

Additionally, the invention relates to the use of a pharmaceutical composition containing at least one compound of 1-[4-(5-cyanoindol-3-yl)butyl]-4-(2-carbamoyl-benzofuran-5-yl)-piperazine and/or one of its biocompatible salts together with at least one solid, liquid or semiliquid excipient or adjunct for the treatment of substance-related disorders.

Thus the invention provides a pharmaceutical preparation for the treatment of substance-related disorders characterized in that it contains at least 1-[4-(5-cyanoindol-3-yl)butyl]-4-(2-carbamoyl-benzofuran-5-yl)-piperazine or one of its pharmaceutically acceptable salts.

The compounds according to the invention are preferably administered in analogy to other known commercially available preparations for the treatment of substance-related disorders (e.g. fluoxetine, fluvoxamine), preferably in doses of between approximately 0.1 and 1000 mg, in particular between 5 and 500 mg per dose unit. The composition may be administered once or more times a day for example 2, 3 or 4 times daily or in sustained release form. The daily dose is preferably between approximately 0.01 and 100 mg/kg of body weight. However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. Oral administration is preferred, but also peroral routes of administration (e.g. intraveneous or transdermal) can be utilized.

Additionally, it has been surprisingly found that 1-[4-(5-cyanoindol-3-yl)butyl]-4-(2-carbamoyl-benzofuran-5-yl)-piperazine also has activity against sexual dysfunctions including premature ejaculation.

Accordingly, the present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of sexual dysfunctions.

The term "premature ejaculation" includes congenital premature ejaculation as well as primary premature ejaculation.

In animal models, various behavioural measures for sexual function can be used in animal models depending on the targeted dysfunction in humans, e.g. reduced libido, anorgasmia, or ejaculation disorders. Measures for sexual activity in animals include fascilitation or prolongation of penile errection, ejaculatory behaviour or frequency of mating behaviour in male rats, or the percentage of receptive behaviours in female rats [e.g.: S. Ahlenius and K. Larsson, Neurochem. Res., 1997, 22:1065-1070; S. Ahlenius and K. Larsson, Psychopharmacology, 1998, 137: 374-382; J. Vega-Matuszcyk et al., Pharmacol. Biochem. Behav., 1998, 60: 527-532; J. M. Cantor et al., Psychopharmacology, 1999; 144: 355-362].

1-[4-(5-cyanoindol-3-yl)butyl]-4-(2-carbamoyl-benzofuran-5-yl)-piperazine or one of its physiologically acceptable salts, in particular 1-[4-(5-cyanoindol-3-yl)butyl]-4-(2-carbamoyl-benzofuran-5-yl)-piperazine hydrochloride, were effective on various measures mentioned before.

A typical clinical study for sexual dysfunctions including premature ejaculation is described in the following.

Twenty (20) male patients aged 18-45 years suffering from major depressive disorder together with a history of sexual dysfunction under treatment with Selective Serotonin Reuptake Inhibitor antidepressants will be treated for a 4 week period with 1-[4-(5-cyanoindol-3-yl)butyl]-4-(2-carbamoyl-benzofuran-5yl)-piperazine or a physiologically acceptable salt thereof. Assessment of sexual function and satisfaction will be evaluated using a series of questions to each patient at weekly intervals. (Ref.: A. Feiger et al., J. Clin. Psychiatry 1996, 57(suppl 2): 53-62.

The invention relates furthermore to the use for the manufacture of a medicament for the treatment of sexual dysfunctions in which the pharmacologically acceptable salt is 1-[4-(5-cyanoindol-3-yl)butyl]-4-(2-carbamoyl-benzofuran-5-yl)-piperazine hydrochloride.

Additionally, the invention relates to the use of a pharmaceutical composition containing at least one compound of 1-[4-(5-cyanoindol-3-yl)butyl]-4-(2-carbamoyl-benzofuran-5-yl)-piperazine and/or one of its biocompatible salts together with at least one solid, liquid or semiliquid excipient or adjunct for the treatment of sexual dysfunctions.

Thus the invention provides a pharmaceutical preparation for the treatment of sexual dysfunctions characterized in that it contains at least 1-[4-(5-cyanoindol-3-yl)butyl]-4-(2-carbamoyl-benzofuran-5-yl)-piperazine or one of its pharmaceutically acceptable salts.

The compounds according to the invention are preferably administered in analogy to other known commercially available preparations for the treatment of sexual dysfunctions including premature ejaculation (e.g. fluoxetine, fluvoxamine), preferably in doses of between approximately 0.1 and 500 mg, in particular between 5 and 300 mg per dose unit. The daily dose is preferably between approximately 5 and 100 mg/kg of body weight for a time period of at least about 3 months, preferably for a time period of at least about 6 months. However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. In some instances the compounds of the present invention are administered chronically as long as the patient remains sexually active. Oral administration is preferred, but also peroral routes of administration (e.g. intraveneous or transdermal) can be utilized.

Additionally, it has been surprisingly found that 1-[4-(5-cyanoindol-3-yl)butyl]-4-(2-carbamoyl-benzofuran-5-yl)-piperazine also has activity against eating disorders including anorexia nervosa and bulimia nervosa and/or obesity.

Accordingly, the present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of eating disorders and/or obesity and/or anorexia.

A typical animal model for eating disorders and/or obesity and/or anorexia is named Cumulative Food Intake according to H. C. Jackson, A. M. Needham, L. J. Hutchins, S. E. Mazurkiewicz, D. J. Heal, Br. J. Pharmacol., 1997, 121: 1758-1762, which can be utilized in various species. Usually, rats or mice are given free access to food, and the development of body weight is measured over time. The test can be performed in both starved and non-starved rats or mice. Moreover, chronic or acute administration of a medication can be investigated.

1-[4-(5-cyanoindol-3-yl)butyl]-4-(2-carbamoyl-benzofuran-5-yl)-piperazine hydrochloride given orally up to 360 mg/kg for 4 consecutive days to rats or mice with free access to food result in a reduced development of body weight at higher doses. On the other hand, the lower doses of up to 50 mg/kg result in increased body weight. A reduced development of body weight was also observed in dogs. Thus, differential effects on body weight indicating therapeutic efficacy in either obesity or anorexia depending on the dose range used are evident.

It is known that serotonin reuptake inhibitors such as fluoxetine, fluvoxamine, paroxetine or sibutramine (e.g. K. Inoue, N. Kiriike, Y. Fujisaki, M. Kurioka, S. Yamagami, Physiol. Behav. 1997, 61: 603-608; R. Ciccocioppo, I Panocka, C. Polidori, C. T. Dourish, M. Massi Psychopharmacology 1997, 134: 55-63; H. C. Jackson, A. M. Needham, L. J. Hutchins, S. E. Mazurkiewicz, D. J. Heal, Br. J. Pharmacol., 1997, 121: 1758-1762; S. Garattini, Obes. Res. 1995, 3 (Suppl 4): 463S-470S) reduce food intake dramatically. Particularly the presynaptic 5-$HT_{1A}$ properties of 1-[4-(5-cyanoindol-3-yl)butyl]-4-(2-carbamoyl-benzofuran-5-yl)-piperazine or one of its physiologically acceptable salts are of interest because these receptors are involved in the inhibition of food intake and potentiate the effects of serotonin reuptake inhibitors in a synergistic way (A. C. Trillat, I. Malagie, M. Mathe-Allainmat, M. C. Anmella, C. Jacquot, M. Langlois, A. M. Gardier, Eur. J. Pharmacol. 1998, 357: 179-84; D. L. Li, R. M. A. Simmons, S. Iyengar, Brain Res. 1998, 781: 119-26). It has been found that a combined selective 5-HT reuptake inhibitor and 5-$HT_{1A}$ receptor like 1-[4-(5-cyanoindol-3-yl)butyl]-4-(2-carbamoyl-benzofuran-5-yl)-piperazine or one of its physiologically acceptable salts which includes both mechanisms leads to therapeutic advantages.

A typical clinical study for anorexia nervosa is described in the following. Twenty (20) female patients aged 18-40 years suffering from anorexia nervosa as diagnosed by DSM-IV will be treated for an 12 week period with either 1-[4-(5-cyanoindol-3-yl)butyl]-4-(2-carbamoyl-benzofuran-5-yl)-piperazine or one of its physiologically acceptable salts or placebo in a double-blind fashion.

Clinical improvement will be assessed by measurements of weight, menstruation status. Depressive symptoms will be assessed by use of the Montgomery Asberg Depression Rating Scale according to S. A. Montgomery et al., British Journal of Psychiatry, 1979, 134: 382-389.

A typical clinical study for bulimia nervosa is described in the following. Twenty (20) female patients aged 18-40 years suffering from bulimia nervosa as diagnosed by DSM-IV will be treated for a 8 week period with either 1-[4-(5-cyanoindol-3-yl)butyl]-4-(2-carbamoyl-benzofuran-5-yl)-piperazine or one of its physiologically acceptable salts or placebo in a double-blind fashion.

Clinical improvement will be assessed by comparison of the frequency of binge-eating and vomiting episodes, and measurements of weight.

Associated symptoms of bulimia nervosa such as depression will be assessed by means of the Montgomery Asberg Depression Rating Scale according to S. A. Montgomery et al., British Journal of Psychiatry, 1979, 134: 382-389.

The invention relates furthermore to the use for the manufacture of a medicament for the treatment of eating disorders and/or obesity and/or anrexia in which the pharmacologically acceptable salt is 1-[4-(5-cyanoindol-3-yl) butyl]-4-(2-carbamoyl-benzofuran-5-yl)-piperazine hydrochloride.

Additionally, the invention relates to the use of a pharmaceutical composition containing at least one compound of 1-[4-(5-cyanoindol-3-yl)butyl]-4-(2-carbamoyl-benzofuran-5-yl)-piperazine and/or one of its biocompatible salts together with at least one solid, liquid or semiliquid excipient or adjunct for the treatment of eating disorders and/or obesity and/or anorexia.

Thus the invention provides a pharmaceutical preparation for the treatment of eating disorders and/or obesity and/or anorexia characterized in that it contains at least 1-[4-(5-cyanoindol-3-yl)butyl]-4-(2-carbamoyl-benzofuran-5-yl)-piperazine or one of its pharmaceutically acceptable salts.

The compounds according to the invention are preferably administered in analogy to other known commercially available preparations for the treatment of eating disorders and/or obesity and/or anrexia (e.g. fluoxetine, fluvoxamine), preferably in doses of between approximately 0.1 and 500 mg, in particular between 5 and 300 mg per dose unit. The daily dose is preferably between approximately 0.01 and 10 mg/kg of body weight However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. Oral administration is preferred, but also peroral routes of administration (e.g. intraveneous or transdermal) can be utilized.

Additionally, it has been surprisingly found that 1-[4-(5-cyanoindol-3-yl)butyl]-4-(2-carbamoyl-benzofuran-5-yl)-piperazine also has activity against fibromyalgia.

Accordingly, the present invention relates to the use of 1-[4-(5-cyanoindol-3-yl)butyl]-4-(2-carbamoyl-benzofuran-5-yl)-piperazine or a physiologically acceptable salt thereof, for the manufacture of a medicament for the treatment of fibromyalgia.

Fibromyalgia, a chronic muscle disorder, is characterized by pain of the whole locomotion system which is not caused by any inflammation or psychological state of the patient combined with chronic fatigue syndrome and multiple tender-points. Further symptoms are disturbance of sleep, morning rigidity, headache, irritable bowel and bladder syndrome, and paresthesias. Patients suffering from fibromyalgia show no increased values of inflammation or increased rheumatoid factors. According to an inquiry in the USA, 2% of the population are affected by fibromyalgia.

In the last years, some characteristics for diagnosis were developped (e.g. M. B. Yunus, Z. Rheumatol 1989, 48: 217-222) to differentiate from overlapping somatic or psychiatric disorders.

The reason for fibromyalgia is unknown but it is shown that the antidepressive drug amitryptiline gave positive results in clinical studies [L. Stander, CNS Drugs 1999, 11: 49-60]. 1-[4-(5-cyanoindol-3-yl)butyl]-4-(2-carbamoyl-benzofuran-5-yl)-piperazine and/or a physiologically acceptable salt thereof show similar influence to the sleep regulatory system but posess no anticholinergic side-effects which are typical for tricyclic antideppressants. Furthermore, it is described that studies of the cerebrospinal fluid support a relationship between serotonin and fibromyalgia in certain areas of the central nervous system [I. J. Russell et al., Arthritis Rheum 1992, 35: 550-556 and E. Houvenagel et al., Rev. Rheum. Mal Osteoartic 1990, 57: 21-23].

Rapid procedures to test pain-relieving properties of drugs are the abdominal constriction (writhing) test according to E. Siegmund et al., Proc. Soc. Exp. Biol. Med. 1957, 95: 729-731 and the intradermal formalin test accorrding to S. Hunskaar et al., J. Neurosci. Meth. 1985, 14: 69-76. For example, 1-[4-(5-cyanoindol-3-yl)butyl]-4-(2-carbamoyl-benzofuran-5-yl)-piperazine hydrochloride at 30 mg/kg p.o. reduced abdominal contrictions by 82%, and 10 mg/kg p.o. reduced the formalin-induced pain response by 79%.

A more sophisticated animal model for fibromyalgia is chronic constrictions of the sciatic nerve in rats associated with hyperalgesia, allodynia and spontaneous pain [G. J. Bennett G. J. and Y. K. Xie, Pain 1988, 33: 87-107]. In this model, rats are anesthesized and 4 ligatures spaced 1 mm apart are loosely tied around the left sciatic nerve. Rats are tested when the chronic state is fully installed, i.e. one week after sciatic nerve surgery, for reactivity to thermal and tactile stimulation. A rat is placed in a box. For thermal stimulation, an infrared radiant source is focused under the non-lesioned and lesioned hindpaws and the hindpaw withdrawal latencies are recorded. For tactile stimulation, the tip of an electronic Von Frey probe is applied with increasing pressure on the non-lesioned and lesioned hindpaws, and the force required to induce a paw-withdrawal is recorded.

A typical clinical study for fibromyalgia is described in the following. Twenty (20) male or female patients aged 18-65 years suffering from fibromyalgia will be treated with 1-[4-(5-cyanoindol-3-yl)butyl]-4-(2-carbamoyl-benzofuran-5-yl)-piperazine or a physiologically acceptable salt thereof for eight weeks in an open label clinical study. Assessment of clinical improvement will be made by means ratings of pain symptoms on a 100 mm Visual Analogue Scale for overall pain, and by the McGill pain questionaire according to R. Meizack, Pain 1987, 30:191-197. Depressive symptoms will be assessed by means of the Montgomery Asberg Depression Rating Scale according to S. A. Montgomery et al., British Journal of Psychiatry, 1979, 134: 382-389 and the Hamilton Depression Rating Scale according to M. Hamilton, Journal of Neurology, Neurosurgery and Psychiatry, 1960, 23: 56-62.

Clinical improvement could be also assessed by means of the number of positive tender points (TP score ≧11 from 18) according to the ACR criteria (Arthritis Rheum. 1990, 33: 160-172) for the diagnosis of fibromyalgia.

The invention relates furthermore to the use for the manufacture of a medicament for the treatment of fibromyalgia in which the pharmacologically acceptable salt is 1-[4-(5-cyanoindol-3-yl)butyl]-4-(2-carbamoyl-benzofuran-5-yl)-piperazine hydrochloride.

Additionally, the invention relates to the use of a pharmaceutical composition containing at least one compound of 1-[4-(5-cyanoindol-3-yl)butyl]-4-(2-carbamoyl-benzofuran-5-yl)-piperazine and/or one of its biocompatible salts together with at least one solid, liquid or semiliquid excipient or adjunct for the treatment of fibromyalgia.

Thus the invention provides a pharmaceutical preparation for the treatment of fibromyalgia characterized in that it contains at least 1-[4-(5-cyanoindol-3-yl)butyl]-4-(2-carbamoyl-benzofuran-5-yl)-piperazine or one of its pharmaceutically acceptable salts.

The compounds according to the invention are preferably administered in analogy to other known commercially available preparations for the treatment of fibromyalgia (e.g. amitryptiline), preferably in doses of between approximately 0.1 and 500 mg, in particular between 5 and 300 mg per dose unit. The daily dose is preferably between approximately 0.01 and 10 mg/kg of body weight. However, the specific dose for each patient depends on all sorts of factors, for example on the activity of the specific compound employed, on the age, body weight, general state of health, sex, on the diet, on the time and route of administration, on the excretion rate, pharmaceutical substance combination and severity of the particular disorder to which the therapy relates. Oral administration is preferred, but also peroral routes of administration (e.g. intraveneous or transdermal) can be utilized.

All the pharmaceutical preparations used for the treatment of sub-type anxiety disorders, bipolar disorders, mania, dementia, substance-related disorders, sexual dysfunctions, eating disorders, obesity, anorexia or fibromyalgia can be used as pharmaceuticals in human or veterinary medicine.

A process for the manufacture of a pharmaceutical preparation used for the treatment of sub-type anxiety disorders, bipolar disorders, mania, dementia, substance-related disorders, sexual dysfunctions, eating disorders, obesity, anorexia or fibromyalgia is characterised in that 1-[4-(5-cyanoindol-3-yl)butyl]-4-(2-carbamoyl-benzofuran-5-yl)-piperazine or one of its pharmaceutically acceptable salts are converted into a suitable dosage form together with at least one solid, liquid or semiliquid excipient or adjunct Suitable excipients are organic or inorganic substances which are suitable for enteral (e.g. oral), parenteral or topical adminstration and which do not react with 1-[4-(5-cyanoindol-3-yl)butyl]-4-(2-carbamoyl-benzofuran-5-yl)-piperazine and/or one of its biocompatible salts, for example water, vegetable oils, benzyl alcohols, alkylene glycols, polyethylene glycols, glycerol triacetate, gelatine, carbohydrates such as lactose or starch, magnesium stearate, talc, petroleum jelly. Forms which are used for oral administration are, in particular, tablets, pills, sugar-coated tablets, capsules, powders, granules, syrups, liquids or drops, forms for rectal administration are, in particular suppositories, forms for parenteral administration are, in particular, solvents, preferably oily or aqueous solutions, furthermore suspensions, emulsions or implants, and forms for topical administration are transdermal plasters, ointments, creams or powders. 1-[4-(5-cyanoindol-3-yl)butyl]-4-(2-carbamoyl-benzofuran-5-yl)-piperazine and/or one of its pharmaceutically acceptable salts may also be lyophilized and the resulting lyophilisates used for example for the preparation of injectable products. The abovementioned preparations can be in sterilized form and/or comprise auxiliaries such as glidants, preservatives, stabilizers and/or wetting agents, emulsifiers, salts for modifying the osmotic pressure, buffer substances, colourings, flavourings and/or other active ingredients, e.g. one or more vitamins.

Preparations may, if desired, be designed to give slow release of 1-[4-(5-cyanoindol-3-yl)butyl]-4-(2-carbamoyl-benzofuran-5-yl)-piperazine or a biocompatible salt thereof.

The examples which follow relate to pharmaceutical products:

EXAMPLE A

Vials

A solution of 100 g of 1-[4-(5-cyanoindol-3-yl)butyl]-4-(2-carbamoyl-benzofuran-5-yl)-piperazine or a physiologically acceptable salt thereof and 5 g of disodium hydrogen phosphate in 3 l of twice-distilled water is brought to pH 6.5 with 2N hydrochloric acid, filter-sterilized, filled into vials, lyophilized under sterile conditions and sealed in sterile form. Each vial comprises 5 mg of active ingredient.

EXAMPLE B

Suppositories

A mixture of 20 g of 1-[4-(5-cyanoindol-3-yl)butyl]-4-(2-carbamoyl-benzofuran-5-yl)-piperazine or a physiologically acceptable salt thereof is melted with 100 g of soya lecithin and 1400 g of cocoa butter, and the mixture is poured into moulds and left to cool. Each suppository comprises 20 mg of active ingredient.

EXAMPLE C

Solution

A solution is prepared from 1 g of 1-[4-(5-cyanoindol-3-yl)butyl]-4-(2-carbamoyl-benzofuran-5-yl)-piperazine or a physiologically acceptable salt thereof, 9.38 g of $NaH_2PO_4.2H_2O$, 28.48 g of $Na_2HPO_4.12H_2O$ and 0.1 g of benzalkonium chloride in 940 ml of twice-distilled water.

The pH is brought to 6.8, and the solution is made up to 1 l and sterilized by irradiation. This solution can be used in the form of eyedrops.

EXAMPLE D

Ointment 500 mg of 1-[4-(5-cyanoindol-3-yl)butyl]-4-(2-carbamoyl-benzofuran-5-yl)-piperazine or a physiologically acceptable salt thereof are mixed with 99.5 g of petroleum jelly under aseptic conditions.

EXAMPLE E

Tablets

A mixture of 1 kg of 1-[4-(5-cyanoindol-3-yl)butyl]-4-(2-carbamoyl-benzofuran-5-yl)-piperazine or a physiologically acceptable salt thereof, 4 kg of lactose, 1.2 kg of potato starch, 0.2 kg of talc and 0.1 kg of magnesium stearate is tableted in the customary manner in such a way that each tablet comprises 10 mg of active ingredient.

EXAMPLE F

Sugar-Coated Tablets

A mixture is tableted analogously to Example E, and the tablets are subsequently coated in the customary manner with a coating of sucrose, potato starch, talc, tragacanth and colouring.

EXAMPLE G

Capsules 2 kg of 1-[4-(5-cyanoindol-3-yl)butyl]-4-(2-carbamoyl-benzofuran-5-yl)-piperazine or a physiologically acceptable salt thereof are filled into hard gelatin capsules in the customary manner so that each capsule comprises 20 mg of the active ingredient.

EXAMPLE H

Ampoules

A solution of 1 kg of 1-[4-(5-cyanoindol-3-yl)butyl]-4-(2-carbamoyl-benzofuran-5-yl)-piperazine or a physiologically acceptable salt thereof in 60 l of twice-distilled water is filter-sterilized, filled into ampoules, lyophilized under sterile conditions and sealed in sterile form. Each ampoule comprises 10 mg of active ingredient.

EXAMPLE I

Spray for Inhalation 14 g of 1-[4-(5-cyanoindol-3-yl)butyl]-4-(2-carbamoyl-benzofuran-5-yl)-piperazine or a physiologically acceptable salt thereof are dissolved in 10 l of isotonic NaCl solution, and the solution is filled into commercially available pump-operated spray containers. The solution can be sprayed into mouth or nose. One actuation (approximately 0.1 ml) corresponds to a dose of approximately 0.14 mg.

The invention claimed is:

1. A method for treating a bipolar disorder, mania or both in a patient in need thereof comprising administering to said patient an effective amount of 1-[4-(5-cyanoindol-3-yl)butyl]-4-(2-carbamoyl-benzofuran-5-yl)-piperazine or a physiologically acceptable salt thereof.

2. A method according to claim 1, wherein said patient is suffering from mania.

3. A method according to claim 1, wherein said patient is administered the pharmacologically acceptable salt is 1-[4-(5-cyanoindol-3-yl)butyl]-4-(2-carbamoyl-benzofuran-5-yl)-piperazine hydrochloride.

4. A method according to claim 1, wherein said patient is administered the pharmacologically acceptable salt is 1-[4-(5-cyanoindol-3-yl)butyl]-4-(2-carbamoyl-benzofuran-5-yl)-piperazine hydrochloride.

5. A method according to claim 2, wherein said patient is administered the pharmacologically acceptable salt is 1-[4-(5-cyanoindol-3-yl)butyl]-4-(2-carbamoyl-benzofuran-5-yl)-piperazine hydrochloride.

6. A method according to claim 1, wherein said patient is suffering from a bipolar disorder.

7. A method according to claim 1, wherein 1-[4-(5-cyanoindol-3-yl)butyl]-4-(2-carbamoyl-benzofuran-5-yl)-piperazine or a physiologically acceptable salt thereof is administered to said patient in a daily amount of 0.01-10 mg/kg of body weight.

8. A method according to claim 7, wherein 1-[4-(5-cyanoindol-3-yl)butyl]-4-(2-carbamoyl-benzofuran-5-yl)-piperazine hydrochloride is administered to said patient in a daily amount of 0.01-10 mg/kg of body weight.

9. A method according to claim 1, wherein 1-[4-(5-cyanoindol-3-yl)butyl]-4-(2-carbamoyl-benzofuran-5-yl)-piperazine or a physiologically acceptable salt thereof is administered to said patient in a dose of 0.1-500 mg.

10. A method according to claim 9, wherein 1-[4-(5-cyanoindol-3-yl)butyl]-4-(2-carbamoyl-benzofuran-5-yl)-piperazine hydrochloride is administered to said patient in a dose of 0.1-500 mg.

11. A method according to claim 1, wherein 1-[4-(5-cyanoindol-3-yl)butyl]-4-(2-carbamoyl-benzofuran-5-yl)-piperazine or a physiologically acceptable salt thereof is administered orally to said patient.

12. A method according to claim 11, wherein 1-[4-(5-cyanoindol-3-yl)butyl]-4-(2-carbamoyl-benzofuran-5-yl)-piperazine hydrochloride is administered orally to said patient.

13. A method according to claim 1, wherein 1-[4-(5-cyanoindol-3-yl)butyl]-4-(2-carbamoyl-benzofuran-5-yl)-piperazine or a physiologically acceptable salt thereof is administered intraveneously to said patient.

14. A method according to claim 1, wherein 1-[4-(5-cyanoindol-3-yl)butyl]-4-(2-carbamoyl-benzofuran-5-yl)-piperazine hydrochloride is administered intraveneously to said patient.

15. A method according to claim 1, wherein 1-[4-(5-cyanoindol-3-yl)butyl]-4-(2-carbamoyl-benzofuran-5-yl)-piperazine or a physiologically acceptable salt thereof is administered transdermally to said patient.

16. A method according to claim 1, wherein 1-[4-(5-cyanoindol-3-yl)butyl]-4-(2-carbamoyl-benzofuran-5-yl)-piperazine hydrochloride is administered transdermally to said patient.

* * * * *